United States Patent [19]

Albarda

[11] 4,300,385
[45] Nov. 17, 1981

[54] METHOD AND APPARATUS FOR DETERMINING THE ALCOHOL CONTENT OF A PERSON'S BLOOD

[75] Inventor: Scato Albarda, Gross Schenkenberg, Fed. Rep. of Germany

[73] Assignee: Drägerwerk Aktiengesellschaft, Fed. Rep. of Germany

[21] Appl. No.: 119,458

[22] Filed: Feb. 7, 1980

[30] Foreign Application Priority Data

Feb. 22, 1979 [DE] Fed. Rep. of Germany ....... 2906832

[51] Int. Cl.³ ............................................. G01N 31/00
[52] U.S. Cl. ...................................................... 73/23
[58] Field of Search .................. 73/23, 27 R, 421.5 R; 422/84; 340/632, 633, 634; 128/719

[56] References Cited

U.S. PATENT DOCUMENTS

| | | | |
|---|---|---|---|
| 3,877,291 | 4/1975 | Hoppesch et al. | 73/27 R |
| 4,090,078 | 5/1978 | Heim | 73/23 |
| 4,163,383 | 8/1979 | VanderSyde et al. | 422/84 |

FOREIGN PATENT DOCUMENTS 2654248  6/1978  Fed. Rep. of Germany .......... 73/23

Primary Examiner—Stephen A. Kreitman
Attorney, Agent, or Firm—McGlew and Tuttle

[57] ABSTRACT

A method for determining the alcohol content of a person's blood by the measurement of the alcohol concentration of a person's breathing air comprises using a breathing tube through which the person breathes which does not permit any inhaling therethrough. An alcoholometer is connected to the tube and a sensor of the meter is disposed in association with the tube so that instant alcohol concentration values are determined. The values which are determined are fed into a holding circuit which feeds these values to an indicator. The indicator is operated so that only alcohol concentration value higher than a previous one is recorded in the indicator. During the entire time of breathing the quantity of breathing air that is passed through the tube is measured and after a quantity which would be sufficient for alcohol content evaluation is reached is the value on the indicator used as an indication of the alcohol concentration. The apparatus associated with the tube advantageously includes in addition to the alcoholometer a gas meter which includes a counter connected to the indicator in holding circuit with suitable lamps or other signals for indicating when the value shown in the indicator obtains the alcohol concentration value.

7 Claims, 1 Drawing Figure

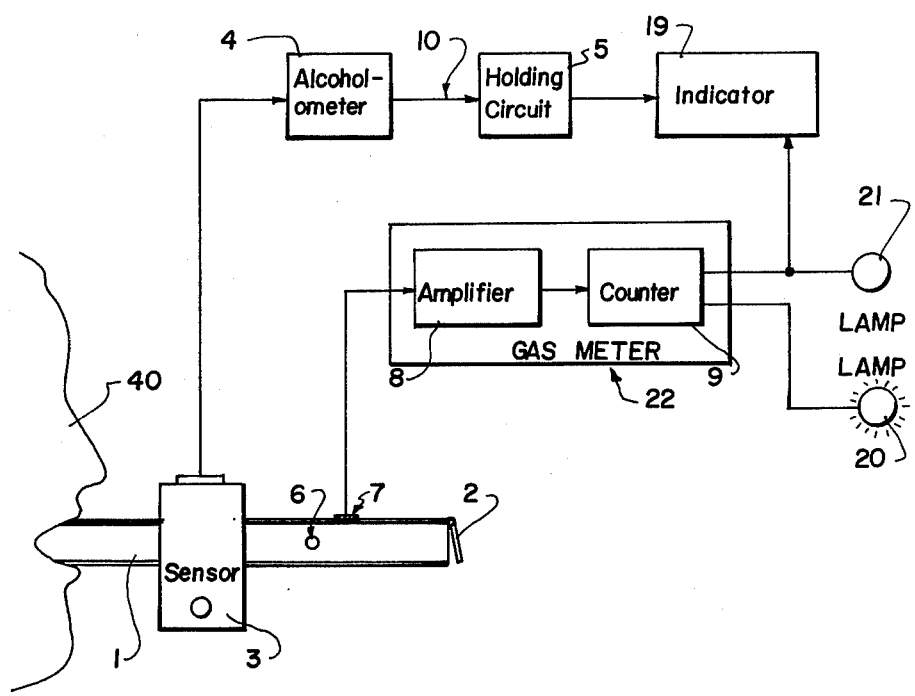

METHOD AND APPARATUS FOR DETERMINING THE ALCOHOL CONTENT OF A PERSON'S BLOOD

FIELD AND BACKGROUND OF THE INVENTION

This invention relates in general to alcohol detection devices and methods, and in particular to a new and useful method for determining the alcohol concentration of the blood by measuring the alcohol concentration of the breathing air of a person.

As a practical matter, it is not possible for a test person whose breath is being collected for alcohol detection to breathe over a longer period of time so shallowly that only the oral cavity and the upper respiratory tracts are ventilated. After about one minute, the lungs require a deep breath. The breathing air exhaled after that is then in equilibrium with the blood alcohol. A measurement with an alcohol-meter then indicates the alcohol content of the blood.

A known arrangement for determining the alcohol concentration of the blood measures the alcohol in the breathing air at a time determined by a time control. This time is determined by the expiration of time predetermined interval starting within the exhaling period. The breathing air throughout must not drop during this period below a given minimum throughput, and must only flow in the exhaling direction. When these two conditions are not met, an error detector determines the invalidity of the measurement.

The given time interval is provided to ensure that the test person has already exhaled the air from the oral cavity and the trachea at the time of measurement, and that the measuring instrument measures the alcohol concentration of the breathing air from the alveoli of the lungs. The expiration of the given time interval is determined by the time at which a minimum amount of breathing air, preferably at least 75% of the total breathing air volume, has been exhaled. An integrator can integrate the breathing air throughout in time during inhalation and exhalation, and determine therefrom the expiration of the time interval after the breathing air minimum volume. The embodiment is to be independent of the physical structure of the test person who may either have a big lung or may not be cooperative. A deliberately flat inhalation may simulate a much too low breathing capacity. The automatically established minimum breathing volume can then in the practical test only be mixed air from the lungs and the oral and larygneal cavity (West German Offenlegungsschrift No. 24 28 353).

Another known method and the respective device or arrangement therefore start from the fact that the true alcohol concentration in the breathing air is only determined if that portion of the exhaled air is tested for its alcohol value that could establish in the alveoli of the lungs equilibrium with the alcohol concentration of the blood. The shuttle air between oral and laryngeal cavity and the mixed air from the alveolar air must therefore, be measured separately.

The method and the respective arrangement solve this problem by means of an infrared measuring instrument which constantly measures the alcohol concentration during the sampling.

A threshold comparator determines the variation of the measured values per unit of time which is a measure for the rate of rise of the alcohol concentration.

A measured value is only transmitted to the indicator when the rate of rise drops below a given threshold value. This first condition results from the fact that the portion of the shuttle air from the oral and laryngeal cavity diminishes constantly with a drop in the rate of rise, and only alveolar air is contained in the measuring channel of the device when it drops below the threshold value. Another condition for transmitting the measured value is that the rate of flow of the exhaling air determined by a flowmeter must have been above a given value during a given time period until the measuring value is transmitted. This second condition measures the provided course of the measuring method. The alcohol concentration is measured by an infrared measuring instrument with a short response time arranged in the breathing air current.

The device is voluminous and complicated due to the requirement of meeting the three conditions, namely determination of the variation in time of the alcohol signal, measurement of the rate of flow of the exhaling air compared to a given value, and minimum maintenance of this value over a given time period, and it requires in addition corresponding monitoring (West German Offenlegungsschrift No. 26 10 578).

SUMMARY OF THE INVENTION

The invention provides a method and an arrangement for determining the alcohol concentration of the blood by measuring the alcohol concentration of the breathing air, where the measuring result is not influenced, even by uncooperative persons, by deceptive maneuvers, e.g. by flat breathing.

This problem as far as it concerns the method, is solved by using a breathing tube having a flow path extending from a mouthpiece (inlet) and to an opposite outlet and through which the person whose breath is to be tested directs his breathing air by breathing into the inlet end and which has an alcoholometer connected thereto for continuously measuring the alcohol concentration and an indicator for indicating this concentration, comprising the steps of directing the breathing air of the person through the tube while preventing any inhaling through the tube, continuously determining the alcohol content of the breathing air with the alcohol meter as it passes through the tube, indicating on the indicator only the highest values of the alcohol which are being determined, continuously totalling the quantity of breathing air passing through the tube, and after a predetermined quantity of the air has passed through the tube using the indicator value as the value of the alcohol concentration according to the characterizing portion of claim 1. This advantageous solution guarantees the recognition of the true alcohol content of the blood with progressing measurement and attaining of the given amount of exhaled air. Deception by unwilling test persons is not possible, because even with deliberately deceptive breathing only in the oral cavity and the upper respiratory ducts, the test person must breathe deep before he reaches the given limiting exhaled air. This is demanded by the body. The constantly measuring highspeed alcoholometer thus determines the breathing alcohol value from the lungs which is in equilibrium with the alcohol content of the blood. This highest measured value is made visible in the indicator over the holding circuit. The blood alcohol content is thus determined in any case until the given limiting value of the exhaled air has been attained.

The solution, as it is represented in the arrangement, solves this problem in a simple manner. As principal elements are required only the obvious alcoholometer and indicator and a gas meter. These are known elements whose mode of operation and reliability of the measured value are known. Both yield in combination a simple device which differs from other known devices in its reliability regarding the determination of the blood alcohol value.

Accordingly, it is an object of the invention to provide a method for determining the alcohol content of a person's blood by measuring the alcohol concentration of a person's breathing air using a breathing tube which is connected to an alcoholometer which permits the passage of the breathing air from a person's mouth and which comprises continuously determining the alcohol content of the breathing air as it passes through the tube indicating on an indicator only the highest of the values of alcohol which are being determined, continuously measuring the quantity of breathing air passing through the tube and after a predetermined quantity of the air has passed through the tube as determined by measurement thereof using the value on the indicator as the value of the alcohol concentration.

A further object of the invention is to provide a device for determining alcohol content of a person's blood which includes a breathing tube having an open end with a non-return valve which permits only exhaling into the breathing tube and which includes a sensor of an alcoholometer for readily determining the alcohol content of the breathing air passing through the tube and further includes a holding circuit connected to an indicator for passing only the excessively highest values of the alcohol content to an indicator and further including means for measuring the breathing air which passes through the tube and after a predetermined amount has passed through the tube providing an indication so that the indicator value may then be read as the determination of the alcohol concentration.

A further object of the invention is to provide a breathing apparatus for determining alcohol content of a person's breath which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWING

The only FIGURE of the drawing is a schematic representation of a person breathing into a breathing tube having an arrangement for the determination of alcohol content of his blood in accordance with the invention.

DESCRIPTION OF THE PREFERRED EMBODIMENT

Referring to the drawing, in particular the invention embodied therein comprises a method and apparatus for determining the alcohol content of a person's blood with a measurement of the alcohol concentration of a person's breathing air. For this purpose a person 40 breathes through an exhaling tube 1 which has a bore with an open inlet end which is closed at its outlet end by a non-return valve so that the person cannot inhale through the tube. In accordance with the method of the invention the person breathes through the tube 1 and the alcohol content thereof is determined by an alcoholometer 4 which includes a sensor 3 associated with the tube. The values of alcohol contencentration in the exhaled air are referred to a holding circuit by a connection 10 to a holding circuit element 5 which permits the recording on an indicator 19 of only the successively higher alcohol values which are determined.

With the method of the invention the amount of breathing gas that is passed through the tube 1 is continuously measured by a gas meter generally designated 22 and when a predetermined quantity of this breathing air has passed through the tube the indicated values shown on the indicator 19 comprises the alcohol concentration value.

The arrangement contains an exhaling tube 1, rigid or flexible, through which the test person exhales. He inhales through his nose. A non-return valve 2 prevents inhalation through exhaling tube 1.

On exhaling tube 1 is arranged a sensor 3 of a high-speed alcoholometer 4 of known design, e.g. an optical-type alcoholometer. The measured value determined by sensor 3 and alcoholometer 4 is fed to a known holding circuit. From here rising measured values which are due to higher breathing alcohol values, are fed to an indicator 19. Lower measured values, compared to the preceding higher values, are retained in holding circuit 5, so that indicator 19 always indicates the respective highest alcohol value.

The total amount of exhaled air is determined and indicated with a gas meter 22, in this embodiment it is a Karman whirl counter with a whirl rod 6 and a feeler 7 designed as a pressure transducer, in or on exhaling tube 1, as well as an amplifier 8 and a counter 9. The counter 9 lights up a yellow lamp 20 as long as the given lower limit value of exhaled air has not yet been attained, (61 is a suitable amount), and a green lamp 21 lights up when the limit value has been attained or exceeded.

While a specific embodiment of the invention has been shown and described in detail to illustrate the application of the principles of the invention, it will be understood that the invention may be embodied otherwise without departing from such principles.

What is claimed is:

1. A method of determining the alcohol content of a person's blood by the measurement of the alcohol concentration of the person's breathing air using a breathing tube having a flow path extending from an inlet end to an opposite outlet end through which the person directs his breathing air by breathing with the inlet end and which has an alcoholometer connected thereto for continuously measuring the alcohol concentration and an indicator for indicating this concentration, comprising directing the breathing air of the person through the tube while preventing any inhaling through the tube, continuously determining the alcohol content of the breathing air with the alcoholometer as it passes through the tube, indicating on the indicator only the highest of the values of alcohol which are being determined, continuously totaling the quantity of breathing air passing through the tube, and after a predetermined quantity of air has passed through the tube using the indicator value as the concentration of alcohol value.

2. A method according to claim 1 wherein a gas meter is used to determine the amount of exhaled air passing through the tube and a signal is connected to the gas meter to indicate a given limiting value of exhaled air has been obtained so that the test is completed and the measured value of the indicator indicates the amount of alcohol in the blood.

3. A method according to claim 2 wherein the alcoholometer which is employed is a known optical instrument and wherein after a predetermined quantity of breathing air is directed through the tube an indicator lamp is lit.

4. A method according to claim 1 wherein the tube includes a non-return valve to prevent inhaling therethrough and the alcoholometer has a sensor connected to the tube further wherein a holding circuit is connected to the alcoholometer so that values of alcohol which are determined are held by the holding circuit and only a value which is higher than any previous value is directed to the indicator.

5. A device for measuring the alcohol concentration of a person's blood comprising a breathing tube having a mouthpiece end conducted to be positioned in a person's mouth and an opposite open end, a non-return valve arranged at the opposite open end preventing inhaling through said tube, an alcoholometer having a sensor connected with said tube for sensing the alcohol content of the breathing air, a holding circuit connected to said alcoholometer receiving the indications of the alcohol content therefrom, an indicator connected to said holding circuit and indicating only an alcohol value which is higher than any previous value received by said holding circuit, and a gas meter having a sensor associated with said tube for sensing the quantity of gas flowing therethrough being connected to said indicator so that said indicator indicates as the alcohol percentage only the highest of the values which have been recorded after a predetermined quantity of gas is passed therethrough.

6. A device according to claim 5 wherein said gas meter comprises a Karman-whirl counter and a whirl rod and includes a sensor comprising a pressure transducer, said counter further including an amplifier and an air quantity counter.

7. A device according to claim 6 wherein said indicator has means for printing the indicated value.

* * * * *